United States Patent
Heaton (10) Patent No.: US 6,522,138 B2
(45) Date of Patent: Feb. 18, 2003

(54) RESOLUTION ENHANCEMENT FOR SEQUENTIAL PHASE ALTERNATED PAIR NUCLEAR MAGNETIC RESONANCE MEASUREMENTS

(75) Inventor: Nicholas J. Heaton, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 09/797,278

(22) Filed: Mar. 1, 2001

(65) Prior Publication Data

US 2001/0035751 A1 Nov. 1, 2001

Related U.S. Application Data

(60) Provisional application No. 60/193,643, filed on Mar. 31, 2000.

(51) Int. Cl.$^7$ ................................................. G01V 3/00
(52) U.S. Cl. ....................................................... 324/303
(58) Field of Search ........................................ 324/303

(56) References Cited

U.S. PATENT DOCUMENTS

| | | | |
|---|---|---|---|
| 5,023,551 A | * 6/1991 | Kleinberg et al. | 324/303 |
| 5,291,137 A | 3/1994 | Freedman | |
| 5,363,041 A | * 11/1994 | Sezginer | 324/300 |
| 5,381,092 A | * 1/1995 | Freedman | 324/303 |
| 6,121,774 A | * 9/2000 | Sun et al. | 324/300 |
| 6,140,817 A | 10/2000 | Flaum et al. | |
| 6,208,136 B1 | * 3/2001 | Smith et al. | 324/300 |
| 6,326,784 B1 | * 12/2001 | Ganesan et al. | 324/303 |
| 6,388,441 B1 | * 5/2002 | Chen | 324/300 |

OTHER PUBLICATIONS

S Meiboom & D Gill, "Modified Spin Echo Method for Measuring Nuclear Relaxation Times," *Review of Scientific Instruments* 29, pp. 688–691 (1958).

D McKeon et al., "An Improved NMR Tool Design for Faster Logging," *SPWLA 40th Annual Logging Symposium*, Paper CC (May 30–Jun. 3, 1999).

* cited by examiner

*Primary Examiner*—Edward Lefkowitz
*Assistant Examiner*—Dixomara Vargas
(74) *Attorney, Agent, or Firm*—Kevin P. McEnancy; Brigitte L. Jeffery; John J. Ryberg (57) ABSTRACT

A method for retrieving corrected individual measurements from a series of sequentially pairwise-combined measurements. The method includes providing an initial estimate for a first one of the corrected individual measurements, deriving temporary estimates for other ones of the corrected individual measurements by subtracting the initial estimate from the first sequentially pairwise-combined measurements to produce an estimate for a second one of the corrected individual measurements, and repeating the subtraction from each of the next sequentially pairwise-combined measurements until temporary estimates for each of the corrected individual measurements are obtained, and correcting errors in the temporary estimates to generate error-corrected estimates by filtering an alternating error component associated with the initial estimate.

30 Claims, 4 Drawing Sheets

RESOLUTION ENHANCEMENT FOR SEQUENTIAL PHASE ALTERNATED PAIR NUCLEAR MAGNETIC RESONANCE MEASUREMENTS

CROSS REFERENCE TO RELATED APPLICATIONS

This application claims priority of U.S. Provisional Application Ser. No. 60/193,643, filed on Mar. 31, 2000.

BACKGROUND OF INVENTION

1. Field of the Invention

The present invention is related to the field of signal processing methods for oil well logging tools. More specifically, the present invention relates to signal processing methods for enhancing the resolution of nuclear magnetic resonance (NMR) measurements.

2. Background Art

Oil well logging tools include nuclear magnetic resonance (NMR) instruments. NMR instruments can be used to determine properties of earth formations, such as the fractional volume of pore space, the fractional volume of mobile fluid filling the pore space, and the porosity of earth formations. General background of NMR well logging is described in U.S. Pat. No. 6,140,817, assigned to the assignee hereof.

A typical NMR logging tool comprises a permanent magnet, which is used to align the nuclei of interest along its magnetic field, and an antenna, which is used to provide radio frequency (RF) pulses and to act as a receiver for the resulting resonance signals. The RF pulses transmitted through the antenna produce a magnetic field which realigns the nuclei in a different orientation. In a typical application, the RF pulse strength is controlled such that the nuclei are realigned onto a plane which is perpendicular to the direction of the magnetic field generated by the permanent magnet.

Such RF pulse is called a 90-degree pulse. Once in this perpendicular plane, the interactions between the static magnetic field and the nuclei cause these nuclei to precess around the static magnetic field axis with a characteristic frequency called Larmor frequency. The precessing of these nuclei produces signals that are detected by the antenna. In the absence of further perturbation, these nuclei will gradually return to their steady state, in which their spins are aligned with the static field generated by the permanent magnet. The process of this return to the steady state is referred to as the spin-lattice relaxation and is defined by a life time called T1. If the nuclei are kept in the perpendicular plane (e.g., by using a series of pulses as in CPMG sequence or a spin-lock sequence), the signals generated by these nuclei will decay exponentially by another mechanism, the spin-spin relaxation, which is defined by a different life time, T2. The T1 and T2 values reflect the chemical and physical properties of the observed nuclei. Therefore, they can provide information as to the properties and the environment of the nuclei.

The signals measured by nuclear magnetic resonance (NMR) logging tools typically arise from the selected nuclei present in the probed volume. Because hydrogen nuclei are the most abundant and easily detectable, most NMR logging tools are tuned to detect hydrogen resonance signals (form either water or hydrocarbons). These hydrogen nuclei have different dynamic properties (e.g., diffusion rate and rotation rate) that are dependent on their environments. The different dynamic properties of these nuclei manifest themselves in different nuclear spin relaxation times (i.e., spin-lattice relaxation time (T1) and spin—spin relaxation time (T2)). For example, Hydrogen nuclei in viscous oils have relatively short relaxation times whereas hydrogen nuclei in light oils possess relatively long relaxation times. Furthermore, the hydrogen nuclei in the free water typically have longer relaxation times than those in the bound water. Consequently, these differing NMR relaxation times can provide information on properties of the earth formations.

Figure 2:
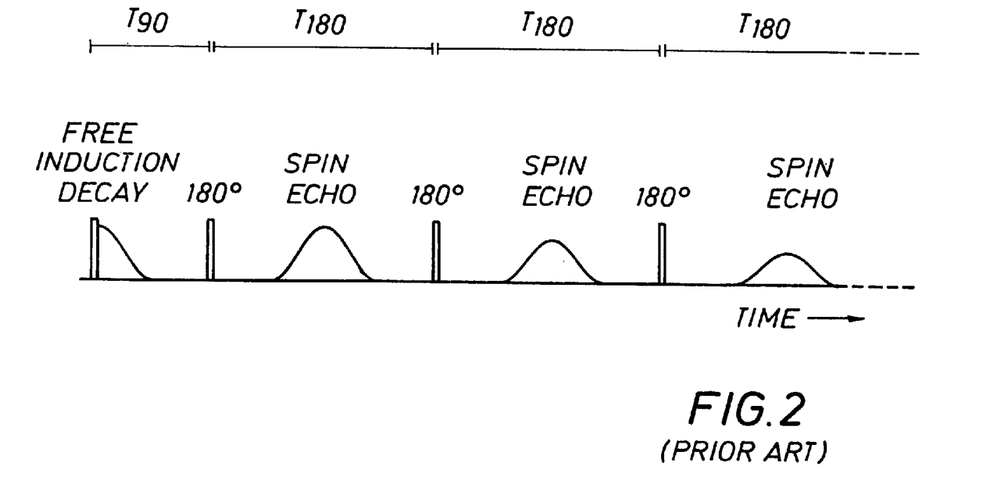
FIG. 2 is a diagram illustrating a conventional type of CPMG pulse sequence.

Most NMR logging tools measure the spin-spin relaxation times (T2) to derive the properties of the earth formations. The T2 relaxation is often measured from a train of spin-echoes that are generated with a series of pulses such as the Carr-Purcell-Meiboom-Gill (CPMG) pulse sequence or some variant of this. The CPMG pulse sequence is well known in the art. [See Meiboom, S., Gill, D., 1958, "Modified Spin Echo Method for Measuring Nuclear Relaxation Times," Review of Scientific Instruments, 29, 688–91]. FIG. 2 shows a CPMG sequence, which is typically composed of a 90-degree pulse followed by a series of 180-degree pulses with a fixed delay time between them. The initial 90-degree pulse aligns the nuclear spins in the plane perpendicular to the magnetic field generated by the permanent magnet. The successive 180-degree pulses keep these spins roughly in this plane for the duration of the measurement The proportion of nuclear spins in the transverse plane decays mainly via the spin—spin relaxation (T2) pathway. Thus, one can derive the T2 relaxation time by analyzing the exponential decay of the spin-echo magnitude.

The fast on-and-off pulses used in the CPMG sequence generate acoustic waves in the antenna by an effect known as the "Lorenz force." The antenna returns to its original shape in a series of damped mechanical oscillations in a process referred to as "magnetoacoustic ringing." Ringing can induce large voltages in the antenna which interfere with the measurement of the voltages induced by the nuclear spins. In addition, the RF pulses can also cause magnetostriction in the permanent magnet, which is a deformation of the magnet. In the process of returning to its original shape, the magnet generates a series of damped mechanical oscillations in a process known as "magnetostrictive ringing." In addition, the antenna/detectors often have inherent electronic offsets, which cause the baseline of the detected signals to deviate from the zero value. In order to cancel the electronic offsets and antenna ringing it is customary to combine two CPMG measurements of opposite phase. These pairwise-combined measurements (herein, measurements denote the detected signal amplitudes) are called phase-alternate-pair (PAP) echo trains and these constitute the datasets that are submitted to processing.

PAPs may be acquired successively or sequentially. In successive acquisition, each measurement consists of a complete PAP measurement, which includes two opposite-phased CPMG measurements, and each PAP measurement is independent of the preceding and the following PAP measurements. The sampling interval (with respect to wellbore length/depth) in successive acquisition is the distance traveled by the NMR logging tool during the acquisition of one complete PAP sequence. Thus, the axial resolution (herein, axial means along the axis of the wellbore) achievable by the successive acquisition method equals the antenna length plus the distance traveled by the NMR logging tool during the acquisition of one PAP sequence.

In contrast, with a sequential acquisition, every individual CPMG measurement contributes to two PAPs. In the first PAP a particular CPMG is combined with its preceding CPMG, which necessarily has opposite phase. In the second PAP it is combined with the following CPMG, which also has opposite phase. [Herein, measurements that are pairwise-combined from sequentially acquired data, like PAP, will be referred to as sequentially pairwise-combined measurements.] The sampling interval (with respect to the wellbore length/depth) in sequential acquisition is the distance traveled by the NMR logging tool during the acquisition of one CPMG sequence, rather than a PAP sequence (which contains two CPMG sequences). Thus, the sampling interval for a sequential acquisition is roughly half that of a successive acquisition. However, the axial resolution of a sequential PAP measurement is identical to that of a successive PAP because it takes two consecutive CPMG data sets to produce a PAP measurement in a sequential acquisition. Sequential PAP acquisition, as implemented on the CMR-PLUS NMR tool, is described in "An Improved NMR Tool Design for Faster Logging," Society of Professional Well Log Analysts (SPWLA) $40^{th}$ Annual Logging Symposium, paper CC (1999).

Although PAP acquisition provides a convenient means for removing electronic offsets and ringing, it degrades the axial resolution of the NMR measurement. This loss of resolution is particularly acute for non-overlapping CPMG measurements, as in the above-described sequential and successive methods. Because it takes two CPMG measurements to produce a PAP measurement in the above-described methods, the axial resolution of a PAP measurement is approximately twice that of each individual CPMG measurement. In situations where thin bed identification and characterization are important, this loss of resolution limits data interpretation. The invention disclosed herein provides a method to recover the axial resolution of NMR data and processed logs from sequential PAP data so that an axial resolution of single CPMG measurements (i.e. one antenna length) is achieved.

A related method for deriving high-resolution permeability estimates from NMR log data is disclosed in U.S. patent application Ser. No. 09/397,581, filed on Sep. 16, 1999, and entitled "Estimating Permeability." The technique involves summing all echoes generated in a CPMG train and applying an empirical calibration of this quantity to derive a permeability estimate. This method provides final logs with effective axial resolution equal to that of the original PAP data.

SUMMARY OF INVENTION

The methods of the present invention relate to methods for retrieving corrected individual measurement from sequentially pairwise-combined measurements. Such sequentially pairwise-combined measurements may include phase-alternated-pair (PAP) NMR measurements from well logging. One of the methods comprises providing an initial estimate for a first one of the corrected individual measurements, deriving temporary estimates for other ones of the corrected individual measurements by subtracting the initial estimate from the first sequentially pairwise-combined measurements to produce an estimate for a second one of the corrected individual measurements, and repeating the subtraction from each of the next sequentially pairwise-combined measurements until temporary estimates for each of the corrected individual measurements are obtained, and correcting errors in the temporary estimates to generate error-corrected estimates by filtering an alternating error component associated with the initial estimate.

Another method is for obtaining resolution-enhanced nuclear magnetic resonance well logging data. The method comprises acquiring individual measurements while moving the nuclear magnetic resonance well logging instrument along the wellbore, combining the individual measurements to form phase-alternated-pair measurements, and solving simultaneous equations to generate error-corrected estimates, wherein the simultaneous equations comprise equations describing the phase-alternated-pair measurements and an additional equation denoting a zero value of a dot product of a vector containing an alternating function and a vector containing the error-corrected estimates.

The methods may be applied to any sequentially pairwise-combined data such as PAP echo data from NMR well logging, or logs derived from these data, to generate a new data set or logs which correspond to single measurements such as the single depth level CPMG measurements from NMR logging, thereby enhancing the resolution of a measurement.

DETAILED DESCRIPTION

Figure 1:
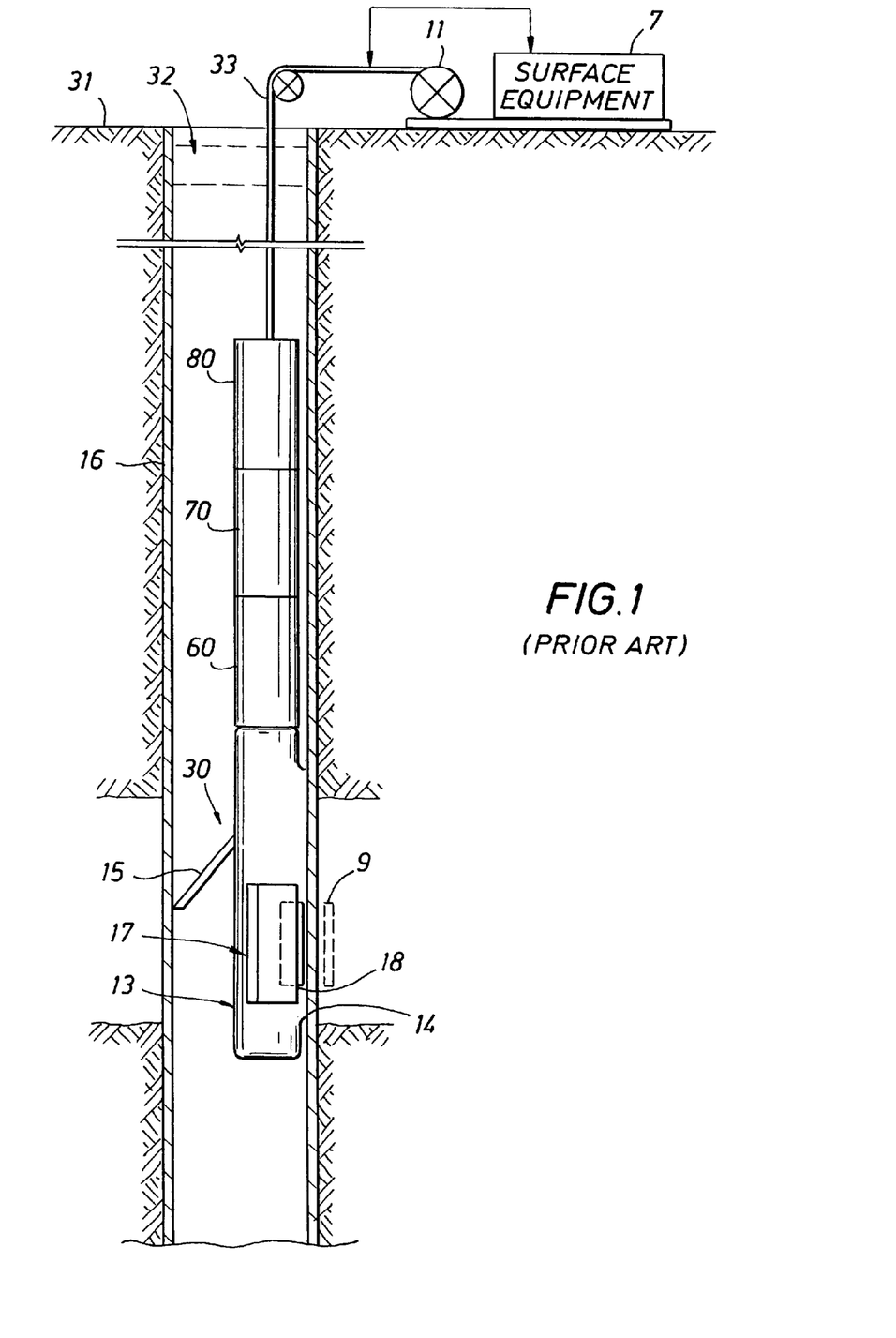
FIG. 1 is a diagram of an NMR well logging apparatus disposed in a wellbore.

Referring to FIG. 1, which shows an apparatus for investigating earth formations 31 traversed by a wellbore 32. It should be noted that FIG. 1 illustrates only one of several types of NMR well logging instruments. The methods of the present invention are not limited to data generated with any specific type of NMR tool. In fact, they are not limited to NMR data at all. Instead, they are generally applicable to any sequentially pairwise-combined data. Therefore, the specific type of NMR instrument shown in FIG. 1 is only for illustration.

In FIG. 1, an NMR well logging tool 30 is suspended in the wellbore 32 on an armored cable 33. As shown in FIG. 1, other logging devices (e.g., density logging, neutron logging, resistivity logging, or sonic devices), illustrated as 60, 70, and 80, can also be incorporated in the logging tool. The length of cable 33 is controlled by suitable means at the surface such as a drum and winch mechanism 11. Other surface equipment, denoted as 7, can include a processor to communicate with the downhole equipment.

The NMR logging tool 30 has a face 14 shaped to intimately contact the borehole wall 16. A retractable arm 15 can be activated to press the body of the tool 13 against the borehole wall during a logging run so that the face 14 is pressed against the wall.

The NMR logging device 30 includes a permanent magnet 17 and an RF antenna 18. The permanent magnet 17 polarizes the nuclei in the earth formation 31 around the NMR logging device 30, while the RF antenna 18 is used to provide a perturbation magnetic field to realign the nuclei in a different orientation. The RF antenna 18 typically does not project the magnetic field far into the earth formations 31. Thus, only those nuclei that are located in a small region close to the wellbore, illustrated as box 9, are measured during NMR logging. The RF antenna 18 also acts as a receiver to detect the NMR resonance signals.

During NMR logging operation, cable 33 is slowly retrieved so that the logging tool 13 travels up the wellbore 32. Note that the logging tool does not have to travel upward. Other types of NMR logging tools (e.g., wireline and while-drilling NMR logging tool) may operate in different manners. The speed at which the logging tool travels is typically determined by the length of the RF antenna 18, the desired axial resolution, and the time it takes to finish an individual NMR measurement sequence. In a typical NMR logging operation, the well is logged at a speed of several hundred to over a thousand feet per hour (about 200–500 meters per hour).

NMR well logging typically measures the T2 relaxation time of hydrogen nuclei in earth formations. The T2 measurements are accomplished by measuring spin echo amplitude in a CPMG pulse sequence as illustrated in FIG. 2. In a CPMG sequence, first RF pulse applied to antenna (18 in FIG. 1) is a 90-degree pulse, which reorients the hydrogen nuclei onto a plane perpendicular to the static magnetic field. Shortly after the initial 90-degree pulse, a train of 180-degree pulses (with a delay time between the successive 180-degree pulses, $T_{180}$, approximately twice as long as the initial delay between the 90-degree and the first 180-degree pulses, $T_{90}$) is applied to the antenna (18 in FIG. 1). Each of these 180-degree pulses results in a spin echo -a growth and subsequent decay of the detected signal magnitudes. In a CPMG measurement, spin—spin relaxation manifests itself as a decay in the magnitude of the detected spin echoes. T2 relaxation time (the spin—spin relaxation lifetime) information is then derived from analysis of the decay profile.

In NMR well logging, the axial resolution of each of the estimates derived from NMR echo data is determined by the total length (axial span along the wellbore) of formation which contributes to the original echo data at the measurement depth. For PAP data, this is equal to the antenna (18 in FIG. 1) length plus the distance the tool moves between successive CPMG measurements. If non-overlapping measurements are made, the axial resolution is about twice the antenna length. If sequential PAPs are acquired, consecutive echo trains are not independent. In fact, each PAP has one CPMG measurement in common with the preceding PAP and another CPMG measurement in common with the following PAP. Using this relationship, it is possible to obtain measurements of formation properties associated with the individual CPMG echo data. The axial resolution of the resulting estimates is just one antenna length.

The basis for one of the methods of the invention is explained as follows. Consider the general case of a series of CPMG measurements in a sequential acquisition. Each echo amplitude at (axial position) depth L, $F_L$, in a CPMG comprises a signal component, $x_L$, a noise component, $\delta_L$, and an offset, $y_L$. Each successive CPMG measurement sequence is acquired with its initial 90-degree pulse in a phase opposite to that of the previous CPMG measurement sequence. Therefore, $F_L = y_L + (-1)^L (x_L + \delta_L)$, where the $(-1)^L$ term represents the alternating phase of the signals. Each CPMG measurement is then combined with the previous one such that the signal components add and the offsets partially cancel to produce a phase-alternated-pair (PAP) measurement, $<X_L>$. Thus, the combined PAP measurement at depth L, $<X_L>$, can be expressed as $$<X_L> = ((-1)^{L-1} F_{L-1} + (-1)^L F_L)/2 = (x_{L-1} + \delta_{L-1} + x_L + \delta_L)/2 + ((-1)^{L-1} y_{L-1} + (-1)^L y_L)/2 \quad (1)$$

If an initial guess (or initial estimate) for $x_0$ ($\tilde{x}_0$) is made, an estimate ($\bar{x}_1$) for $x_1$, i.e., an individual measurement at L=1, can then be calculated according to the following equation:

$$\bar{x}_1 = 2<X_1> - x\tilde{x}_0 = x_0 - \tilde{x}_0 + x_1 + \delta_0 + \delta_1 + y_0 - y_1. \quad (2)$$

As will be shown in later discussion, accuracy of this initial estimate is not important. An initial estimate could be generated ab initio using a computer and a suitable program to give a simulated CPMG measurement. Alternatively, a baseline-corrected (to remove receiver offset) CPMG measurement acquired under similar conditions (i.e., same pulse sequence, same delays, and same number of data points in each measurement) can be used as an initial estimate. Baseline correction of a CPMG measurement can be accomplished by: (1) extrapolating the spin-echo train in the CPMG measurement to infinite time such that no spin-echo is discernable and a constant amplitude remains; and (2) subtracting this constant amplitude from each data point of the CPMG measurement. Using the individual estimate for $x_1$ ($\bar{x}_1$), a similar estimate for $x_2$ ($\bar{x}_2$) can be obtained as follows:

$$\bar{x}_2 = 2<X_2> - \bar{x}_1 = \tilde{x}_0 - x_0 + x_2 - \delta_0 + \delta_2 - y_0 + y_2 \quad (3)$$

Similarly, the individual estimate for $x_L$ ($\bar{x}_L$) at depth L is $$\bar{x}_L = 2<X_L> - \bar{x}_{L-1} = x_L + \delta_L + (-1)^L \Delta_0 + (-1)^L \Psi_L, \quad (4)$$

where $\Delta_0$ is a constant error associated with the initial estimate for $x_0$ and includes an average offset, $\bar{y}$, $$\Delta_0 = \tilde{x}_0 - x_0 - \delta_0 - \Psi_0, \quad (5)$$

and $\Psi_L$ is the offset deviation from its average value $\bar{y}$, $$\Psi_L = y_L - \bar{y}. \quad (6)$$

Thus, each successive estimate (which is a temporary estimate) obtained by this method carries an error that arises from inaccuracy of the initial estimate. This initial error ($\Delta_0 = \tilde{x}_0 - x_0 - \delta_0 - \Psi_0$) either adds to or subtracts from the true measurement in an alternating fashion. Because this error is of the same magnitude and with an alternating phase between each successive estimate, it can be removed by "filtering" to give the corrected estimates for the quantities of interest, $x_L$.

The "filtering" of the initial error is achieved as follows. After successive subtraction according to the above-described method, the estimated measurement, $\bar{x}$, is obtained as a function of depth, L, (L=0, 1, 2, 3 . . . ). The estimate $\bar{x}$ can be rewritten as a linear combination of orthogonal functions, $F_i(L)$, $$\bar{x}_L = \sum_i a_i F_i(L) \quad (7)$$

Because $F_i(L)$ are orthogonal functions, there exists a orthonornality condition:

$$\sum_L F_j(L) F_i(L) = \delta_{ij} \quad (8)$$

where $\delta_{ij}=1$, if i=j, and $\delta_{ij}=0$, otherwise. Note that the summation here is over depth, L, not the function index, i.

In equation (7) the alternating term containing the initial error $(\Delta_0=\tilde{x}_0-x_0-\delta_0-\Psi_0)$, can be represented as the first term, $a_1F_1(L)$, for convenience. Then, $a_1$ represents a constant magnitude of the error and $F_1(L)$ represents the alternating function. If K is defined as an alternating function, which is also a function of depth, L, $$K(L)=(-1)^L. \quad (9)$$

Then, this K function defines an alternating function that is "in phase" with the alternating initial error. Thus, K can be used to represent $F_1(L)$. However, in order to satisfy the orthonormality condition of equation (8), it is necessary to normalize, K, $$F_1(L) = \left(\frac{1}{\sqrt{N}}\right)K(L) \quad (10)$$

If $\bar{x}^*_L$ represents an estimate without the alternating initial error, then:

$$\bar{x}^*_L = \bar{x}_L - a_1F_1(L). \quad (11)$$

To accomplish this subtraction, it is necessary to compute the amplitude $a_1$. The amplitude $a_1$ can be derived from equation (7), bearing in mind the orthonormality condition of equation (8):

$$a_1 = \sum_{L=1}^{N} F_1(L)\bar{x}_L = \sum_{L=1}^{N}\left(\frac{1}{\sqrt{N}}\right)K(L)\bar{x}_L \quad (12)$$

$$\text{Thus, } a_1F_1(L) = \left(\frac{\sum_J \bar{x}_J K(J)}{N}\right)K(L) \quad (13)$$

Combining equations (11) and (13) will produce the corrected measurement, $\bar{x}^*_L$, which is conveniently expressed in a vector notation:

$$\bar{x}^* = \bar{x} - \left(\frac{\bar{x} \cdot K}{N}\right)K \quad (14)$$

where $\bar{x}^*$ contains the corrected values, $\bar{x}$ has elements $\bar{x}_L$, and K is a vector with elements $K(L)=(-1)^L$. Thus, equation (14) provides final estimates (error-corrected estimates or estimates for the corrected individual measurements) of the single depth level measurements that are independent of errors associated with the initial estimate, $\tilde{x}_0$.

An alternative method for arriving at the same solutions is possible. This method relies on solving N+1 simultaneous equations using either matrix operation or any other suitable mathematical operations. The general principle of this approach is as follows.

The relationship between N PAP measurements, $<X_L>$, and the constituent single level (CPMG) estimates, $x_L$, may be summarized by a set of coupled equations $$\langle X_L \rangle = \frac{x_{L-1} + x_L}{2} \quad (15)$$

which are essentially equivalent to equation (1). This system of equations cannot be solved uniquely since there are N+1 unknowns $x_L$ and only N equations. In the derivation outlined above, a particular solution was obtained by arbitrarily choosing an initial guess value for $x_0$, using this to obtain a stepwise solution to successive equations and then filtering the resulting estimates. The same result could also be achieved by combining the filter expression, $$\sum_L x_L K(L) = 0 \quad (16)$$

with equation (15) and then using a standard matrix solution, or any other suitable technique, to solve the N+1×N+1 system of equations. One skilled in the art would appreciate that the methods of the present invention include both the stepwise method as set forth above and the method of solving simultaneous equations.

For large values of N (the number of PAP measurements or depth levels), the statistical error in the final estimates $\bar{x}^*_L$ derives primarily from the uncertainty, $\delta_L$, in the Lth measurement. The standard deviation of $\delta_L$ is $\sqrt{2}\sigma$, where $\sigma$ is the standard deviation of the noise associated with the averaged measurement, $<x_L>$. A systematic error, corresponding to the alternating component of the true values, $x_L$, may be introduced as a result of the "filtering" operation because any alternating component of the true value might be treated as the alternating error. However, in real earth formations, porosity fluctuations are highly irregular and the error produced by removal of a high-frequency periodic component should be relatively small. Equation (14) also suggests that the magnitude of the error decreases with increasing N, the number of depth levels or PAP measurements.

Figure 3:
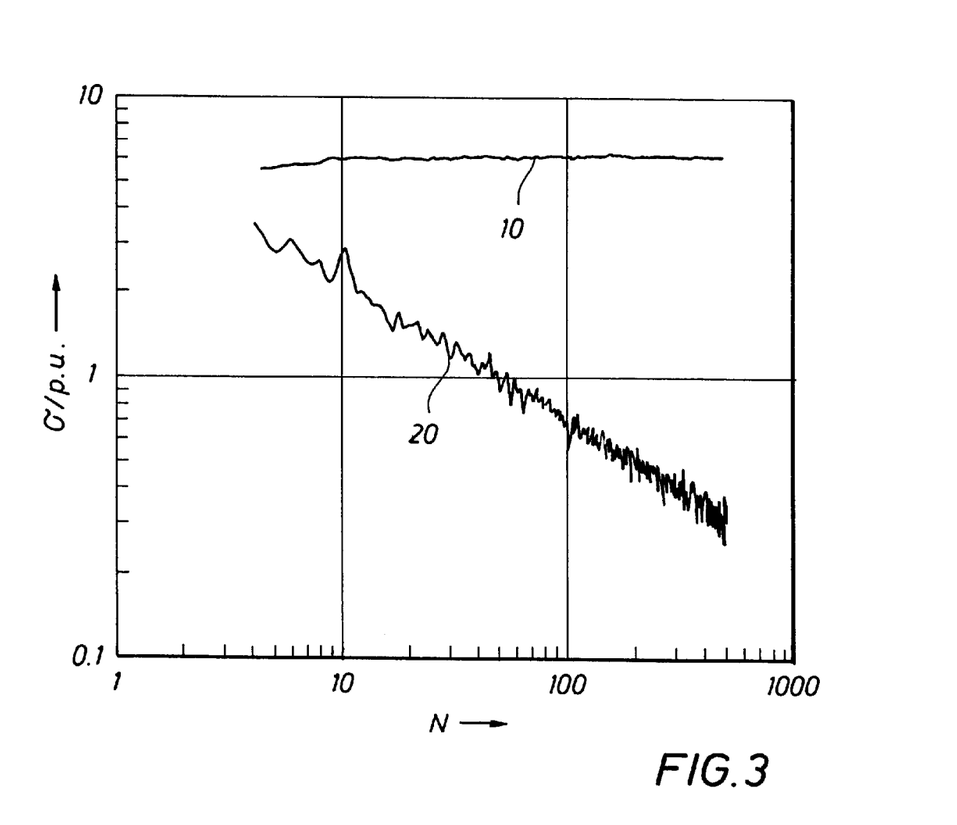
FIG. 3 is a chart illustrating the relationship between the RMS errors in porosity estimates and the number of samples using the methods of the present invention as compared with traditional PAP method.

The effect of the sample size N on the magnitude of the error is illustrated in FIG. 3, which shows the absolute RMS errors in porosity estimates, computed for a series of random formations, as a function of the number of samples (between 4 and 500). The true single depth level porosity values were generated randomly with a uniform distribution between 0 p.u. and 30 p.u. For each independent set of N formation porosities, (N−1) PAP data were computed. From these (N−1) PAP data, N single depth level data were regenerated using the methods of the present invention. The formation porosities were then derived from the PAP or the enhanced single depth level data. The absolute RMS errors represent the standard deviations in the differences between the input porosities and the PAP or the single depth level estimates. For these random formations, the RMS error in the single depth level estimates (curve 20 in FIG. 3) is proportional to $N^{-1/2}$. In contrast, the RMS error in the PAP estimates (curve 10 in FIG. 3) does not decrease with increasing N.

The methods of the invention are applicable to raw echo data or any other quantity that is a linear function of the echo amplitudes. It may also be applied to quantities that are approximately linear functions of the echo amplitudes, such as the porosity, bound-fluid and free-fluid volume estimates derived from the processed PAP echo data. In this case, it may be necessary to limit N such that errors due to non-linearity of the logs with respect to echo amplitudes do not accumulate.

The methods of the invention have been tested using simulated data. $T_2$ distributions and echo trains were generated at regular intervals of 6 inches along a simulated wellbore. In the simulated data, each $T_2$ distribution comprises a bound-fluid peak, with $T_2$ values ranging from 0.3 ms to 20 ms, and a free-fluid peak, with $T_2$ values between 70 ms and 700 ms. The ratio of the peak amplitudes varies between 0.1 and 10 with a periodicity of 15 inches. This periodicity corresponds to laminations of about 7.5 inches thick arranged in an alternating manner. Random, zero-mean noise of 3.5 p.u. per echo was added to each simulated echo train. Successive echo trains were then combined sequentially to generate the simulated PAP data with an effective axial resolution of 12 inches. Porosity, bound-fluid and free-fluid estimates were obtained from this averaged PAP data at each depth by standard inversion. Any of the inversion methods known in the art is suitable. For example, U.S. Pat. No. 5,291,137, issued to Freedman and assigned to the same assignee hereof, discloses a "windows" processing method. For comparison, these same PAP data were subject to the resolution enhancement methods of the present invention before inversion to derive the porosity, bound-fluid and free-fluid estimates.

Figure 4:
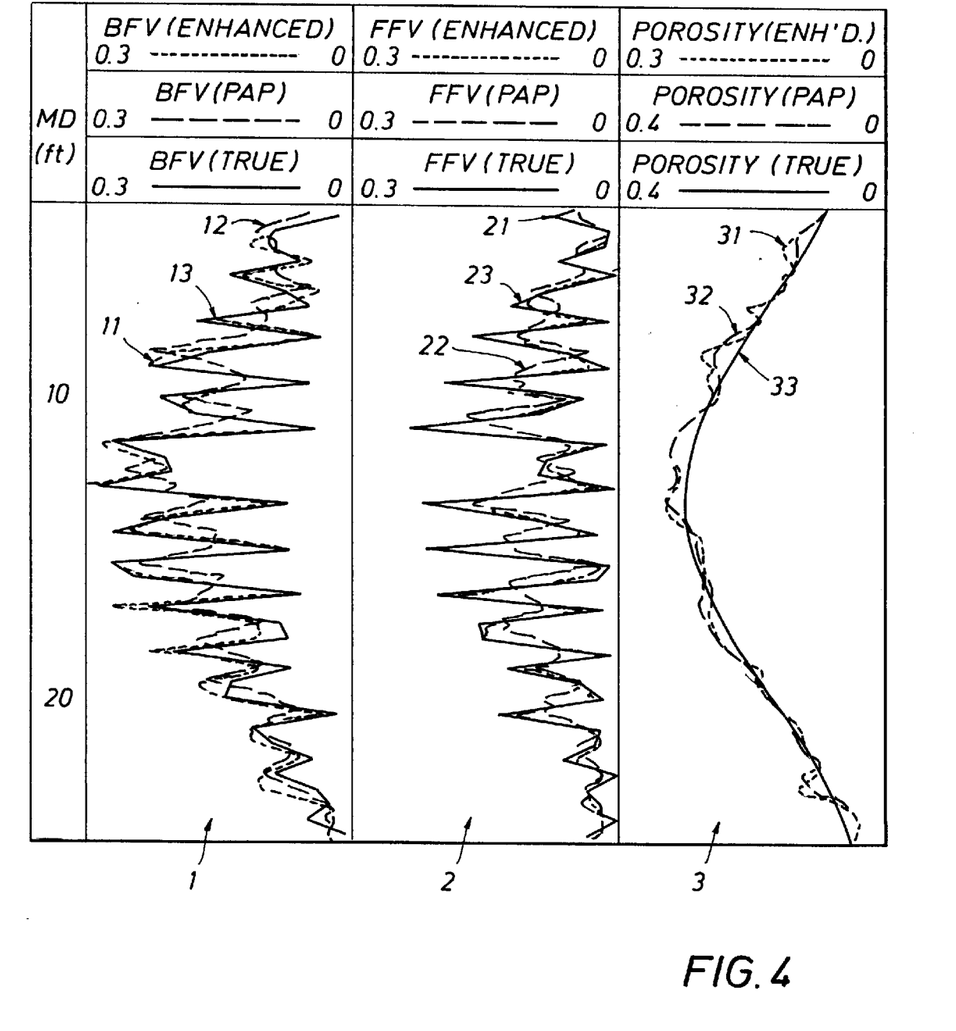
FIG. 4 shows the simulated results of bound-fluid volume, free-fluid volume, and porosity estimates using the methods of the present invention as compared with the traditional PAP method.

The results from this simulation are shown in FIG. 4, in which bound-fluid volume, free-fluid volume, and total porosity estimates are shown in Tracks 1, 2, and 3, respectively. A track, as known in the art, corresponds to one section in the figure illustrating one earth formation property derived from well logging data (see FIG. 4). For bound-fluid (Track 1) and free-fluid (Track 2) volumes, it is clear that single depth level estimates (dotted curves, 11 and 21), which are derived from the resolution enhanced data using the methods of the present invention, correlate much better with the input values (solid curves, 13 and 23) than do the original estimates from the PAP data (dashed curves, 12 and 22).

The total porosity curves vary more slowly (Track 3) than those for fluid volumes (Track 1 and 2). In Track 3, the true porosity is shown as a solid curve, 33. The resolution enhanced estimates for porosity is shown as the dotted curve 31, while that from PAP estimate is shown as the dashed curve 32. Although the resolution enhanced estimate (dotted curve 31) is not significantly better than that derived from the traditional PAP approach (dashed curve 32), no significant artifacts are introduced into the single depth level total porosity estimate. Note that the single depth level estimates were derived entirely from the PAP data without any other input. Therefore, there is no need to alter any currently employed NMR logging method to take advantage of the present invention.

Figure 5:
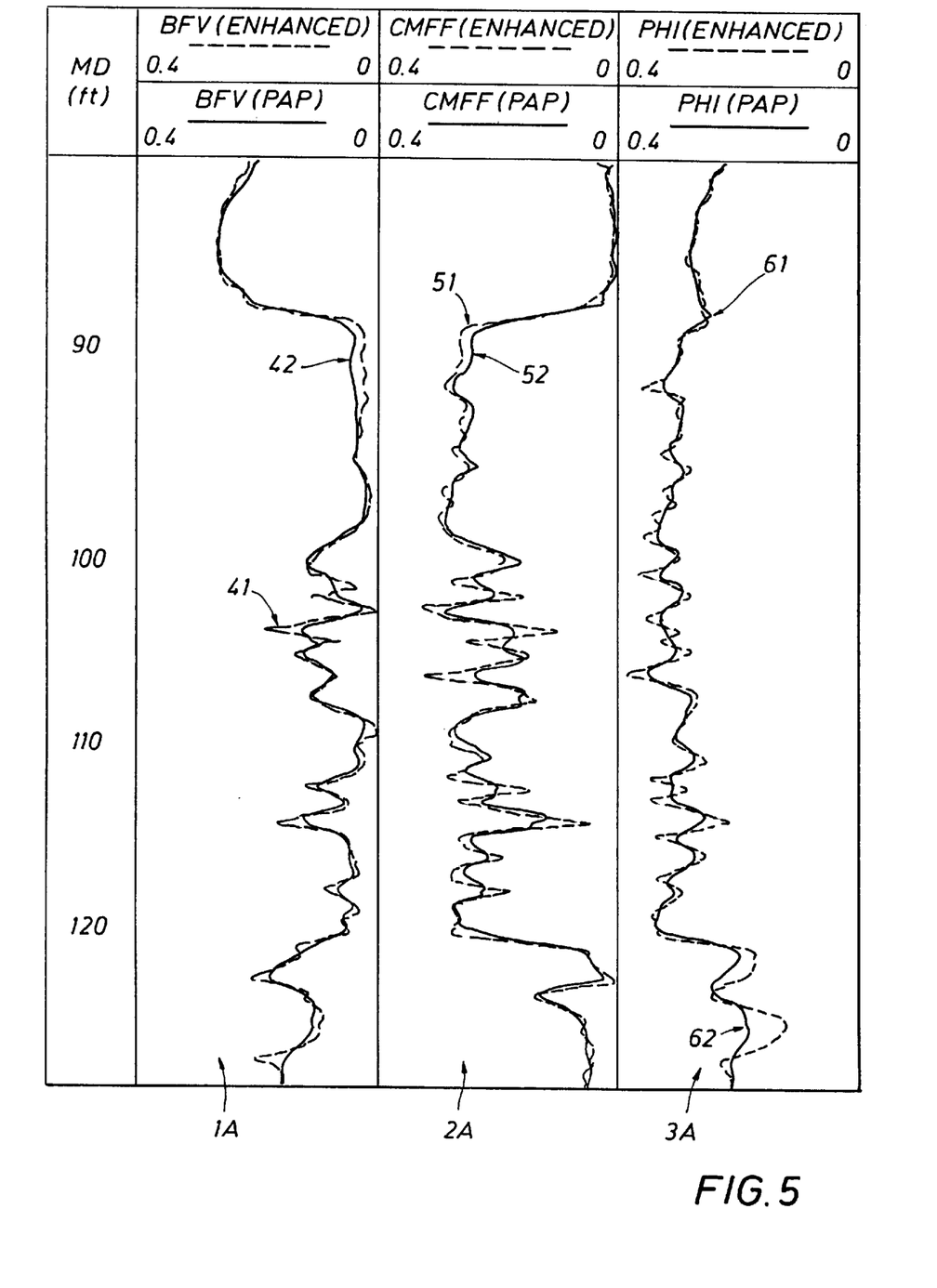
FIG. 5 shows the results from an actual well logs, illustrating the results of using the methods of the present invention as compare to the traditional PAP method in deriving the bound-fluid volume, free-fluid volume, and porosity estimates.

The utility of the methods of the present invention is further illustrated with data measured by an actual NMR logging instrument in an actual wellbore, as shown in FIG. 5. The data used to generate the plot of FIG. 5 were made using an NMR tool sold under trade name CMR-PLUS* by Schlumberger Technology Corporation and were logged at 1200 ft/hr with sequential PAP acquisition. Tracks 1A to 3A compare the standard bound-fluid, free-fluid and total porosity logs, processed using the PAP estimates with an axial resolution of 14 inches (solid curves, 42, 52, and 62, in Tracks 1A–3A, respectively) and single depth level CPMG estimates with an axial resolution of 7 inches (dotted curves, 41, 51, and 61, in Tracks 1A–3A, respectively). The single depth level CPMG estimates were generated using the resolution enhancement methods of the present invention. Note the significant increase in fluctuation of the single depth level bound-fluid and free-fluid curve compared with the PAP estimates. This is most striking over the section from 100 ft to 120 ft, where the FMI image (not shown) indicates some fine laminations. The fluctuations in free-fluid and bound-fluid that appear in this section correlate very well with the laminations in the FMI, indicating that these are not artifacts of the processing. Note also that the bound-fluid and free-fluid curves, which are effectively independent measurements, display a high degree of anticorrelation. This is typical of sand-shale laminations and lends further confidence to the accuracy of the resolution-enhancement method.

While the invention has been described using PAP measurements derived from CPMG measurements, those skilled in the art, having benefit of this disclosure, will appreciate that the methods can be applied to other pairwise-combined data without departing from the scope of the invention as disclosed herein. Accordingly, the scope of the invention should be limited only by the attached claims.

What is claimed is:

1. A method for retrieving corrected individual measurements from a series of sequentially pairwise-combined measurements obtained from an nuclear magnetic resonance logging tool comprising:

providing an initial estimate for a first one of the corrected individual measurements;

deriving temporary estimates from other ones of the corrected individual measurement by subtracting the initial estimate from the first sequentially pairwise-combined measurements to produce an estimate for a second one of the corrected individual measurements, and representing the subtraction from each of the next sequentially pairwise-combined measurement until temporary estimates from each of the corrected individual measurement are obtained; and correcting errors in the temporary estimates to generate error-corrected estimates by filtering an alternating error component associated with the initial estimate.

2. The method of claim 1, wherein the sequentially pairwise-combined measurements comprise phase-alternated-pair nuclear magnetic resonance measurements.

3. The method of claim 2, wherein the nuclear magnetic resonance measurements are obtained by moving a nuclear magnetic resonance well logging instrument along a wellbore drilled through earth formations.

4. The method of claim 2, wherein the phase-alternated-pair nuclear resonance measurements are derived from Carr-Purcell-Meiboom-Gill measurements.

5. The method of claim 4, wherein the initial estimate comprises a baseline-corrected Carr-Purcell-Meiboom-Gill measurement.

6. The method of claim 1, further comprising deriving a value of at least one earth formation property using the error-corrected estimates.

7. The method of claim 6, wherein the at least one earth formation property comprises at least one selected from bound-fluid volume, free-fluid volume, and porosity.

8. A method for obtaining resolution-enhanced nuclear magnetic resonance well logging data comprising:

acquiring individual measurements while moving a nuclear magnetic resonance well logging instrument along a wellbore;

combining the individual measurements to form the phase-alternated-pair measurements;

providing an initial estimate for a first one of the corrected individual measurements used to form the phase-alternated-pair measurements;

deriving temporary estimates for other ones of the corrected individual measurements by subtracting the initial estimate from the first one of the sequentially pairwise-combined measurements to produce an estimate for a second one of the individual measurements, and repeating the subtraction from each of the next sequentially pairwise-combined measurements until temporary estimates for each of the individual measurements are obtained; and correcting errors in the temporary estimates to generate error-corrected estimates by filtering an alternating error component associated with the initial estimate.

9. The method of claim 8, further comprising deriving a value of at least one earth formation property using the error-corrected estimates.

10. The method of claim 9, wherein the at least one earth formation property comprises at least one selected from bound-fluid volume, free-fluid volume, and porosity.

11. The method of claim 8, wherein the individual measurements comprise individual Carr-Purcell-Meiboom-Gill measurements.

12. The method of claim 11, wherein the initial estimate comprises a baseline-corrected Carr-Purcell-Meiboom-Gill measurement.

13. A method for retrieving corrected individual measurements from a series or sequentially pairwise-combined measurements comprising:

obtaining the sequentially pairwise-combined measurements from a nuclear magnetic resonance logging tool;

solving simultaneous equations to generate error-corrected estimates, wherein the simultaneous equations comprise equation s describing the sequentially pairwise-combined measurements and an additional equation denoting a zero value of a dot product of a vector containing an alternating function and a vector containing the error-corrected estimates.

14. The method of claim 13, wherein the sequentially pairwise-combined measurements comprise phase-alternated-pair nuclear magnetic resonance measurements.

15. The method of claim 14, wherein the nuclear magnetic resonance measurements are obtained by moving a nuclear magnetic resonance well logging instrument along a wellbore drilled through earth formations.

16. The method of claim 14, wherein the phase-alternated-pair nuclear resonance measurements are derived from individual Carr-Purcell-Meiboom-Gill measurements.

17. The method of claim 16, wherein the initial estimate comprises a baseline-corrected Carr-Purcell-Meiboom-Gill measurement.

18. The method of claim 13, further comprising deriving a value of at least one earth formation property using the error-corrected estimates.

19. The method of claim 18, wherein the at least one earth formation property comprises at least one selected from bound-fluid volume, free-fluid volume, and porosity.

20. A method for obtaining resolution-enhanced nuclear magnetic resonance well logging data comprising:

acquiring individual measurements while moving the nuclear magnetic resonance well logging instrument along the wellbore;

combining the individual measurements to form phase-alternated-pair measurements; and solving simultaneous equations to generate error-corrected estimates, wherein the simultaneous equations comprise equations describing the phase-alternated-pair measurements as a combination of their respective corrected individual measurements and an additional equation denoting a zero value of a dot product of a vector containing an alternating function and a vector containing the error-corrected estimates.

21. The method of claim 20, further comprising deriving a value of at least one earth formation property using the error-corrected estimates.

22. The method of claim 21, wherein the at least one earth formation property comprises at least one selected from bound-fluid volume, free-fluid volume, and porosity.

23. The method of claim 20, wherein the individual measurements comprise individual Carr-Purcell-Meiboom-Gill measurements.

24. The method of claim 23, wherein the initial estimate comprises a baseline-corrected Carr-Purcell-Meiboom-Gill measurement.

25. A method for obtaining resolution-enhanced nuclear magnetic resonance well logging data comprising:

acquiring individual measurements while moving a nuclear magnetic resonance well logging instrument along a wellbore;

combining the individual measurements to form phase-alternated-pair measurements;

providing an initial estimate for a first one of a plurality of corrected individual measurements;

deriving temporary estimates for other ones of the corrected individual measurements; and correcting errors in the temporary estimates to generate error-corrected estimates by filtering an alternating error component associated with the initial estimate.

26. The method of claim 25, further comprising deriving a value of at least one earth formation property using the error-corrected estimates.

27. The method of claim 26, wherein the at least one earth formation property comprises at least one selected from bound-fluid volume, free-fluid volume, and porosity.

28. The method of claim 25, wherein the individual measurements comprise individual Carr-Purcell-Meiboom-Gill measurements.

29. The method of claim 25, wherein the initial estimate comprises a baseline-corrected Carr-Purcell-Meiboom-Gill measurement.

30. The method as defined in claim 25, wherein the deriving the temporary estimates for the other ones of the corrected individual measurements comprises subtracting the initial estimate from the first one of the sequentially pairwise-combined measurements to produce an estimate for a second one of the corrected individual measurements, and repeating the subtraction from each of the next sequentially pairwise-combined measurements until temporary estimates for each of the corrected individual measurements are obtained.

* * * * *